United States Patent [19]
Spanondis

[11] 3,939,853
[45] Feb. 24, 1976

[54] DENTAL FLOSSER
[76] Inventor: Michael E. Spanondis, 685 Hope St., Tarpon Springs, Fla. 33589
[22] Filed: Sept. 4, 1974
[21] Appl. No.: 503,171

[52] U.S. Cl. ................................................. 132/91
[51] Int. Cl.² ........................................... A61C 15/00
[58] Field of Search ............. 132/91, 92 A, 92 R, 90

[56] References Cited
UNITED STATES PATENTS

| | | | |
|---|---|---|---|
| 788,947 | 5/1905 | Roth | 132/91 |
| 2,187,899 | 1/1940 | Henne | 132/91 |
| 2,233,936 | 3/1941 | Campbell | 132/92 A |
| 2,376,750 | 5/1945 | Bell | 132/92 R |
| 2,492,291 | 12/1949 | Johnson | 132/92 R |
| 2,644,469 | 7/1953 | Cohen | 132/92 R |
| 3,472,247 | 10/1969 | Borsum et al. | 132/91 |
| 3,814,114 | 6/1974 | Roberts | 132/92 A |

*Primary Examiner*—G. E. McNeill
*Attorney, Agent, or Firm*—W. Dexter Brooks

[57] ABSTRACT

A Dental Flosser is described wherein an elongated handle is provided at one end with a bifurcated flosser head including a pair of downwardly extending, spaced and curved arms having concaved and notched extremities to receive a length of dental floss and at the opposite end with the usual tufts of teeth brushing bristles, whereby the one end of the device can be provided with a length of dental floss for use in cleaning food particles and dental plaque from the opposed faces of adjacent teeth, below the free gum margin, and along the margins of dental restorations, and detecting incipient decay of the teeth, and whereby the opposite end can be used for brushing and cleaning the teeth in the usual manner. At the base of the bifurcated head, the device includes a unique floss anchoring button on the top surface and a bulbed fulcrum portion on the bottom surface. The interior tip surface portions of the spaced arms are flared outwardly for safety purposes and protect the gums from injury while the length of floss bridging the bifurcations is engaged between adjacent teeth during the cleaning operation. The spaced arms are further provided with a reduced cross-section adjacent to the base of the bifurcated head to provide more flexibility of the arms and thus, allow a more efficient and complete cleaning of the teeth. Diagonal grooves are provided on the exterior surface of the spaced arms to guide and support the dental floss when it is threaded through the Dental Flosser.

9 Claims, 10 Drawing Figures

DENTAL FLOSSER

BACKGROUND OF THE INVENTION

The present invention relates to a novel dental flosser adapted for manual use in cleaning the opposed faces of adjacent teeth and dental restorations of food particles and dental plaque, and detecting incipient decay of the teeth, the same comprising an elongated handle having at one end, a bifurcated flosser head including a pair of downwardly extending, spaced and curved arms having concaved and notched extremities to receive a length of dental floss and at the opposite end, the usual tufts of teeth brushing bristles. The handle portion may include a centrally located cavity that is adapted to receive a removable floss spool assembly. At the base of the bifurcated head, the dental flosser includes a unique floss anchoring button on the top surface and a bulbed fulcrum portion on the bottom surface. The interior tip surface portions of the spaced arms are flared outwardly for safety purposes and protect the gums from injury while the length of the floss bridging the bifurcations is engaged between adjacent teeth during the cleaning operation. The bulbed fulcrum portions allow the bifurcated end to be fulcrumed on the face of an adjacent tooth of a back molar to thereby permit the dental flosser to reach and effectively clean the back molars. In lieu of or in addition to the removable floss spool assembly, the dental flosser may embody an interior fluid line having an opening directly above the flossing element to allow simultaneous and combined action of the flosser and hydraulic pressure when the fluid line is connected to a fluid source.

Heretofore, dental floss holders of the same general type have been found undesirable and unacceptable due to sundry reasons, including, inter alia, their bulky size, insufficient cleaning and removal of debris and tendency to injure or cut the gums when the flossing element is engaged between or manipulated around adjacent teeth.

At least two considerations are of utmost importance in effectively cleaning the mouth. The first consideration deals with food particles and other debris that become lodged around the teeth. The second consideration involves dental plaque which becomes attached to and forms a coating upon the teeth. In both cases, the foreign matter (i.e., food particles, debris and dental plaque) must be removed for effective cleaning of the teeth.

Dental debris is usually caused by chewing action whereby food particles and juices broken up during mastication are lodged in cavities and spaces about the teeth. Generally this debris is loosely packed and can be removed by such well known devices as the toothbrush, dental floss or by hydraulic means. Directing a stream of water with sufficient pressure to those areas in which the dental debris is located will sometimes be sufficient to dislodge the debris.

Dental plaque which is a complex bacterial type coating attached to a tooth is much more difficult to remove than dental debris. Removal entails something more than a jet or spray of water and will usually require some type of mechanical action. Such mechanical action is best afforded today by a toothbrush scrubbing the external and lingual surfaces of the teeth. Dental plaque which is attached to the interproximal tooth surfaces is currently best removed by dental floss, or other means which have the ability to get between the teeth and mechanically engage the plaque and forcibly rub it off the tooth surfaces.

The recommended procedure for scrubbing the teeth with dental floss on all sides, and particularly below the gum line and between the teeth is to slip the floss between two teeth, hold the floss in a taut loop around about half of the side of a tooth, and reciprocate the floss in a seesaw manner across the tooth while at the same time moving the floss from the bottom of the tooth to the top. This procedure is repeated for the front and back of each tooth so that scrubbing is accomplished from bottom to top all the way around the tooth.

At the present time such flossing is accomplished by holding the floss with the fingers. This requires considerable dexterity and time. Moreover, it is necessary to insert one and sometimes at least two fingers in the mouth in order to accomplish the proper movement on all the teeth. This is quite difficult to accomplish and moreover the fingers obstruct vision so that flossing is not always accomplished in the desired manner.

Various dental floss holders have been provided in the past for using floss to remove food particles from between the teeth. However, because the above described technique for flossing the teeth is a recent development, holders heretofore provided are not suitable for accomplishing all the desired movements of the floss. Moreover, such holders are bulky in size, difficult to use without injuring or cutting the gums when the flossing element is manipulated around adjacent teeth, and fail to effectively clean back molars.

Insofar as hydraulic devices, the prior art has numerous examples of water spray devices for the purpose of directing a flow of liquid into the mouth. Certain drawbacks, however, become immediately apparent such as the fact that the water spray alone can only do part of an effective cleaning job because it is able only to remove the debris which is loosely situated on and between the teeth. The water spray devices will not be effective in cleaning dental plaque nor in cleaning debris which may have lodged more securely between the teeth since they fail to mechanically engage the dental plaque. Devices having only a weak single spray will be insufficient to even clean the loose debris from between the teeth; conversely, those devices which have a harder spray or jet produce physical displeasures which unfortunately make their use undesirable and even act as a deterrent to the use of hydraulic cleaning devices. The major disadvantages inherent in the single jet dental nozzle is the inability of the user to confine the water jet to the dental structures. This results in impingement of the single jet stream upon the soft tissues of the floor of the mouth, tongue, cheeks, or throat which in turn results in such undesirable side effects as pain, gagging, nausea and even vomiting. Another drawback of the prior art devices is that they are not adapted to be used with other cleaning devices nor are they particularly adapted for use within a time element normally considered sufficient for cleaning the mouth.

Accordingly, there is a need in the industry for a dental flosser, preferably of simple construction, easy to use, inexpensive, capable of removing debris and dental plaque from between the teeth in a safe and reliable fashion, and adaptable to auxiliary dental care attachments, such as a Water Pik, electric toothbrush assembly, polishing element or mirror.

OBJECTS OF INVENTION

An object of the present invention is to provide an improved dental flosser of convenient size to be held in the hand while applying dental floss to the teeth and which is simple and durable in construction, economical to manufacture, efficient and sanitary in use, and neat and attractive in appearance.

Another object of the present invention is to provide an improved dental flosser which offers an effective cleaning mechanism without the usually accompanying pain or nuisance to the user.

Another object of the present invention is to provide an improved dental flosser of the character having a handle provided at one end with a unique bifurcated flosser head including a pair of downwardly extending, spaced and curved arms having concaved and notched extremities to receive a length of dental floss and at the opposite end with the usual tufts of teeth brushing bristles, whereby the device can be initially used in the usual manner as a toothbrush, and thereafter as a flosser device to remove debris and dental plaque from the teeth.

Another object of the present invention is to provide an improved dental flosser, wherein a unique scrubbing element can be easily and quickly slipped over the bifurcated ends of a flosser head, the latter being made flexible and drawn together when the scrubbing element is fitted on the bifurcated ends so that the scrubbing element becomes tightly stretched and securely positioned in the flosser head when the bifurcated ends are released.

A further object of the present invention is to provide an improved dental flosser of the character having a bifurcated flosser head including an improved slit configuration at the outer front end of each bifurcation, and a unique floss anchoring button at the base thereof to positively hold dental floss in tension and without slippage while in use, thereby rendering the dental flosser effective for the purposes already set out, with the additional function of permitting a light massaging of the interdental papillea.

A further object of the present invention is to provide an improved dental flosser of the character having a bifurcated flosser head including a bulbed fulcrum portion to allow the bifurcated end to be fulcrumed on the face of an adjacent tooth to the back molar to thereby permit the dental flosser to reach back molars and the back-side of the last molar, thereby rendering the dental flosser effective for the purposes already set out, with the additional function of protecting the gums from injury during the fulcruming and cleaning operation.

Another object of the present invention is to provide an improved dental flosser of the type having a bifurcated flosser head, wherein the spaced bifurcated ends define a gap across which is adapted to span a length of dental floss, the ends of which floss are anchored to a button at the base of the bifurcated head, and wherein the interior tip surface portions of the bifurcated ends are flared outwardly for safety purposes and function in a fashion to protect the gums from injury while the length of floss bridging the bifurcations is engaged between adjacent teeth during the cleaning operation.

A further object of the present invention is to provide an improved dental flosser which successfully incorporates and combines a mechanical and hydraulic cleaning action in one simple-to-use apparatus.

A further object of the present invention is to provide an improved dental flosser which is inexpensive, but yet effective and relatively simple to use, as well as interchangeable with and attachable to other dental care accessories.

These, other, and further objects, important features, and advantages of the present invention to which attention has not been specifically directed hereinbefore, will be better understood and appreciated by those skilled in the art from the following detailed description of the invention taken in conjunction with the acccompanying drawings.

BRIEF DESCRIPTION OF DRAWINGS

The present invention will now be described by way of example, with reference to the accompanying drawings, in which.

DETAILED DESCRIPTION OF INVENTION

Figure 1:
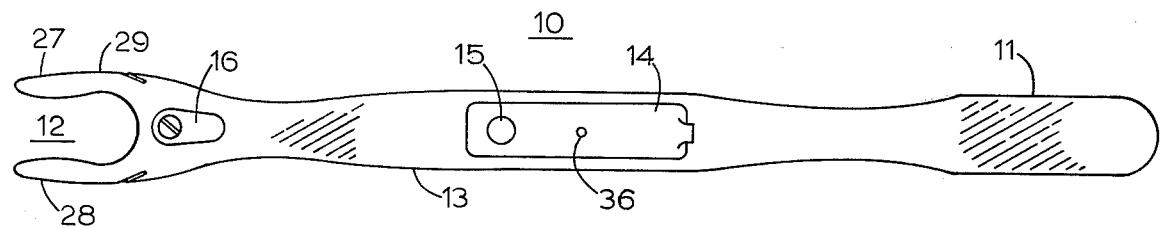
FIG. 1 is a top plan view of the dental flosser without the dental floss threaded therein for use.

The dental flosser 10 provided by this invention and illustrated in the drawings includes generally an elongated handle 13, preferably formed of a suitable transparent material, such as synthetic resin plastic which is preferably of one piece construction and in general is no larger than the standard size toothbrush in normal use. The elongated handle 13 is provided at one end with a bifurcated flosser head 12 and at the opposite end with the usual tufts of teeth brushing bristles 11, whereby the one end 12 of the device can be provided with a length of dental floss 37 for use in cleaning food particles and dental plaque from the opposed faces of adjacent teeth, below the free gum margin, along the margins of dental restorations, and detecting incipient decay of the teeth, and whereby the opposite end 11 can be used for brushing and cleaning the teeth in the usual manner.

Figure 2:
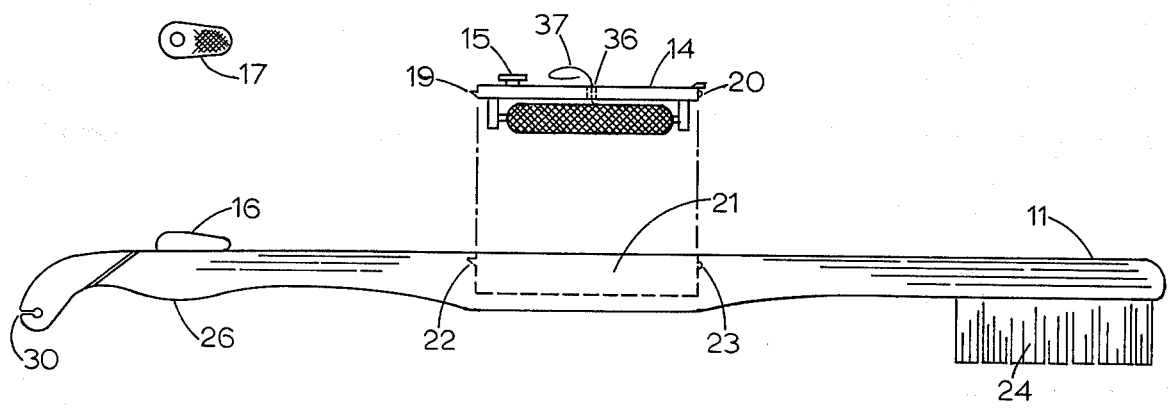
FIG. 2 is a side elevation view of the dental flosser, showing the bifurcated flosser head in conjunction with a toothbrush head, and further illustrates the underside of the floss anchoring button and the removable floss spool assembly.
Figures 3, 4:
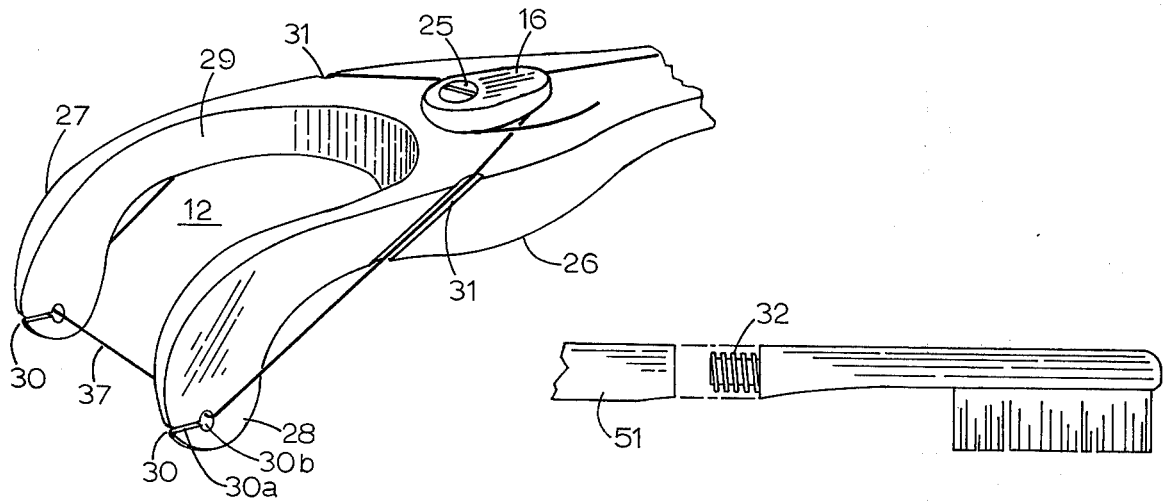
FIG. 3 is a perspective view of the bifurcated flosser head, showing the dental floss threaded therein for use.
FIG. 4 is a fragmentary side view of the toothbrush head of a modified dental flosser in accordance with this invention.

Referring to FIGS. 1–3, the bifurcated flosser head 12 is shown as including a pair of downwardly extending, spaced and curved arms 27 and 28 having concaved and notched extremeties 30 which are adapted to receive a length of dental floss 37 for use in cleaning and removing debris from the teeth. The notched extremeties 30 are more clearly shown in FIGS. 2–3 and each comprises a slit 30a at the outer front end of the spaced arms 27 and 28 which terminates at its inner end in an enlargement 30b. These notched extremeties 30 enable one to thread and install the dental floss 37 through the spaced arms 27 and 28 quickly and with relative ease. Moreover, by positioning the slit 30a at the outer front end of the spaced arms 27 and 28, the user of the dental flosser is able to reciprocate the device in an up and down or rotational fashion in relation to the teeth without releasing the floss from the enlargement 30b. At the base of the bifurcated head 12, the device includes a floss anchoring button 16 which may be secured to the base of the bifurcated head 12 by any known securing means, such as a screw member 25, as illustrated in FIG. 3. The underside surface of the button 16, as shown in FIG. 2, is tapered outward from its center and provided with a scored surface 17 to positively hold the dental floss 37 taut and without slippage while the dental flosser is in use.

As shown in FIG. 2, the elongated handle 13 is provided with a centrally located cavity 70 for a removable floss spool assembly 14 disposed therein. The removable floss spool assembly 14 includes a detachable lid member having a pair of projections on opposite ends of the underside surface of the lid. These projections are adapted to receive a spool or bobbin of dental floss 37 and thus, allow the entire removable floss spool assembly 14 to be replaced as a complete package. At the respective ends of the detachable lid, protrusions 19 and 20 are integrally formed thereon to provide an efficient securing means for the assembly 14. These protrusions 19 and 20 are adaptable to being secured within indentations 22 and 23 which are formed at the respective ends of the centrally located cavity as shown in FIG. 2. The exploded view of the assembly 14 in FIG. 2 illustrates the floss 37 as being withdrawn through the opening 36 in the detachable lid and subsequently tied around knob 15 prior to being threaded through the bifurcated flosser head 12. While the dental flosser 10 is illustrated as including removable floss spool assembly 14, it should be understood that this assembly 14 could be eliminated and the user could use the dental flosser by merely taking a strand of dental floss, quickly inserting it through the notched extremities 30 and tightly securing both ends of the floss by wrapping both ends once around the same side of the floss anchoring button 16 and pulling the floss tightly transverse to the longitudinal axis of the dental flosser. As heretofore described, the floss anchoring button 16 embodies a unique under surface which allows one to positively hold the dental floss 37 in tension and without slippage by merely wrapping it once around the botton 16. This is primarily due to the scored and tapered undersurface which cooperates with the top surface of the elongated handle 13 to tightly secure the dental floss 37 for use.

Figure 5:
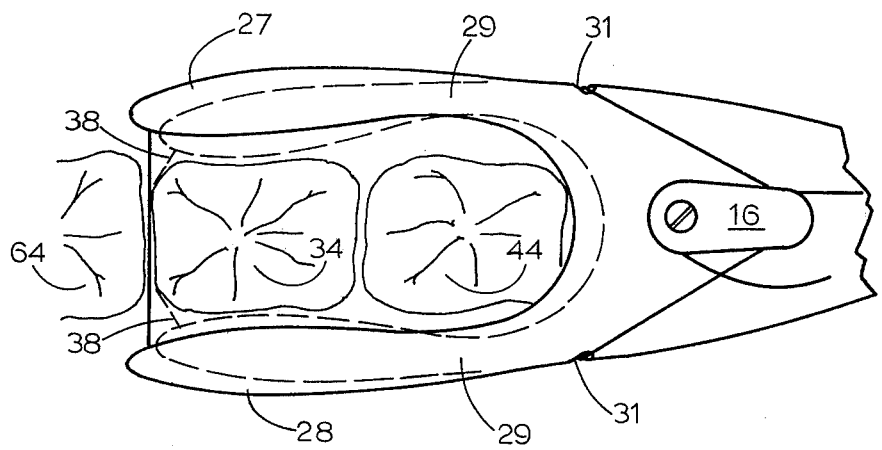
FIG. 5 is a fragmentary top view of the bifurcated flosser head illustrated in FIG. 1, wherein the flexibility features of the spaced arms are shown in typical use with a series of teeth and further, wherein the dental floss is depicted as cleaning the edges of the teeth when the dental flosser is moved along the longitudinal path of the teeth.
Figure 6:
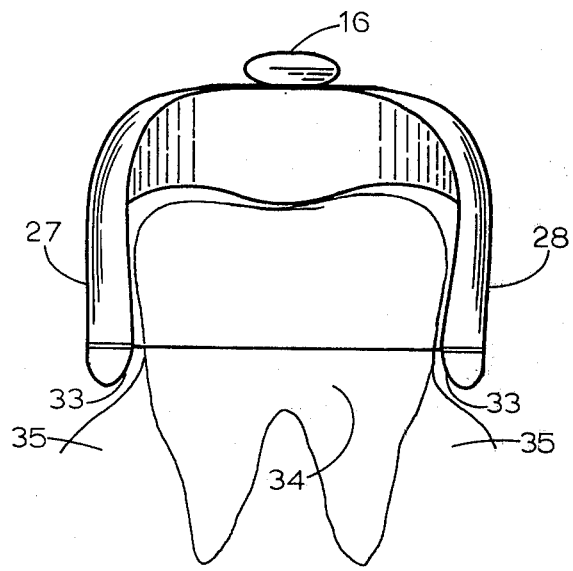
FIG. 6 is a fragmentary end view of the bifurcated flosser head of FIG. 1, wherein the spaced and curved arms are more clearly shown in typical use with a series of teeth, and illustrates the interior tip surface portions of the arms as being flared outwardly to avoid injury to the gums.
Figure 7:
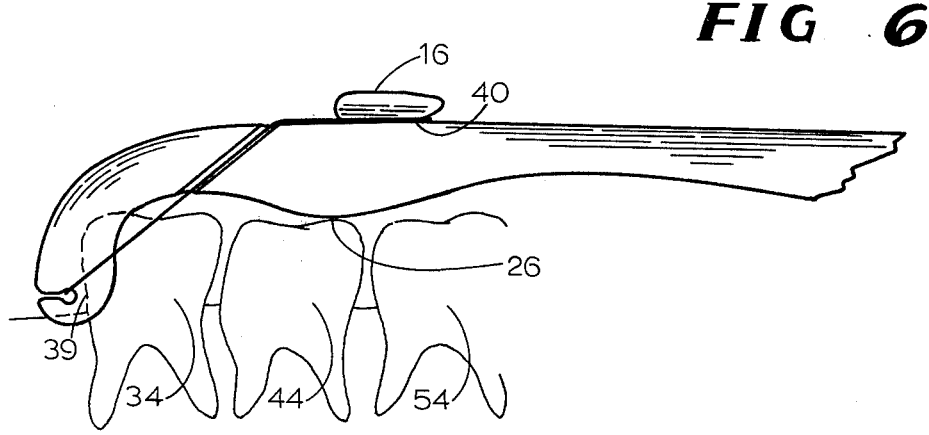
FIG. 7 is a fragmentary side elevation view of the bifurcated flosser head of FIG. 1, wherein the bulbed fulcrum portion is more clearly shown in typical use with a series of teeth, and illustrates the effective cleaning of back molars.

On the bottom side of the elongated handle 13, is a bulbed fulcrum 26 shown more particularly in FIGS. 2, 3 and 7, comprising an integral bulbed protrusion having an arcuate outer face, said fulcrum portion being directly disposed on the opposite face of the elongated handle 13 from the floss anchoring button 16. Referring now to FIGS. 6 and 7, in a typical operation, the bulbed fulcrum portion 26 is seated upon a tooth 44 adjacent the tooth 34 to be cleaned. The fulcrum portion 26 is allowed to rock in an up and down or rotational fashion on the tooth 44 such that the dental floss 37 projects downwardly to clean the entire surface 39 above and below the free gum margin. This is extremely useful for the cleaning of back molars and particularly, the last molar which is hard to reach. During cleaning, the user is able to grip the elongated handle 13 and cause the bridging portion of floss 37 to enter the space between adjacent teeth 34 and 64 so that the floss may be worked up and down or across the teeth as desired. Because of the unique design of the fulcrum portion 26, one is able to use the device with a high degree of care and avoid injury to the gums 35 adjacent the teeth to be cleaned. As shown more particularly in FIG. 6, the interior tip surface portions 33 of the spaced arms 27 and 28 are flared outwardly from the longitudinal axis of the device for safety purposes and to protect the gums 35 from injury while the length of floss 37 bridging the bifurcation is engaged between the adjacent teeth 34 and 64 during the cleaning oepration. The spaced arms 27 and 28 are further provided with a reduced cross-section 29 adjacent to the base of the bifurcated head 12 to provide more flexibility of the arms 27 and 28 and thus, allowing more efficient and complete cleaning of the teeth. This improved cleaning results since, as illustrated in FIG. 5, when one pushes the dental flosser 10 forward or backwards along the teeth line, the taut dental floss 37 being engaged between adjacent teeth 34 and 64 causes the arms 27 and 28 to assume a new location 29. In the position 29, the floss 37 is allowed to encircle the outer edges of the tooth 34 and thus clean a greater surface area of the tooth than by merely reciprocating the flosser 10 in an up and down fashion. While FIG. 5 illustrates the flosser when it is moved in a backward fashion, it should be apparent that when the flosser 10 is moved forward, the floss 37 encircles the outer edges of the tooth 64, and not the tooth 34. Diagonal grooves 31 are provided on the exterior surface of the spaced arms 27 and 28 to guide and support the dental floss when in use. While these grooves 31 are not essential, they are included in the preferred embodiment.

The toothbrush portion 11 may be secured in any convenient manner to the elongated handle 13 and for this purpose, as shown in FIG. 4, there is provided an threaded stud embeded in the plastic handle 13 for cooperation with a corresponding interior threaded portion 32 of the tooothbrush portion 11. This alternative embodiment allows one to adapt the dental flosser to many auxiliary dental cleaning attachments, such as a polishing element, mirror or rubber tipped massaging element, all of which would have a threaded portion 32.

Figure 8:
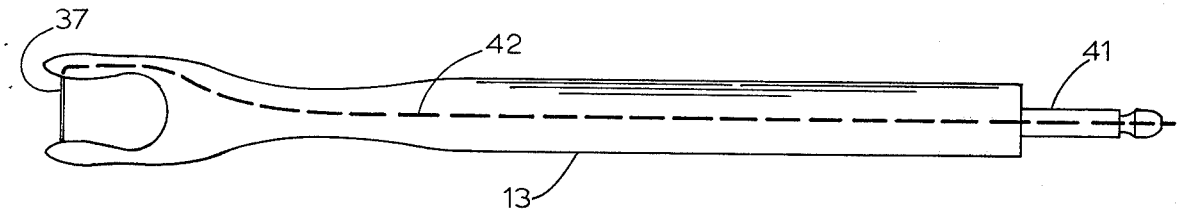
FIG. 8 is a top plan view of another embodiment of the dental flosser, wherein a fluid line is shown for connection to a fluid source.
Figure 10:
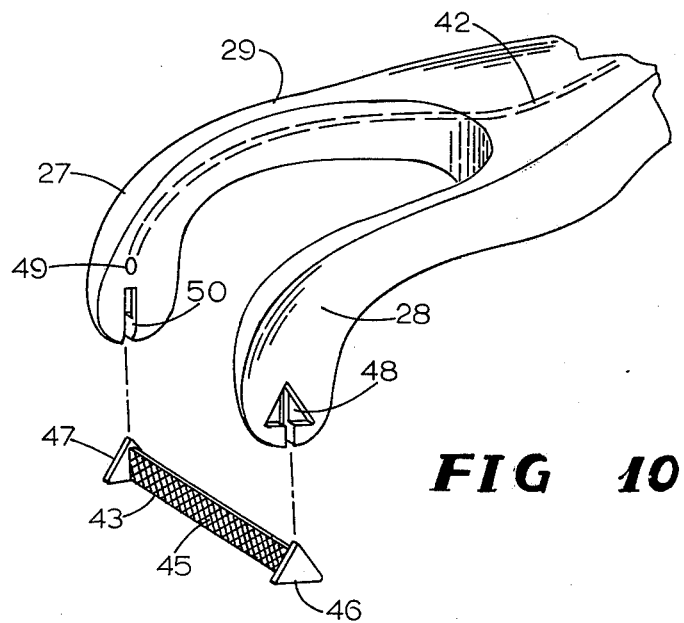
FIG. 10 is a fragmentary perspective end view of the bifurcated flosser head of FIG. 9 wherein the side recessed indentations are more clearly shown as receiving the mechanical scrubbing element and further illustrates the use of a fluid line in conjunction with the mechanical scrubbing element.

Now describing the modification shown in FIG. 8, the elongated handle 13 is shown as being provided with a longitudinal cavity 42 which functions as a fluid line, in which event, an opening 49 is provided directly above the cleansing element, such as illustrated in FIG. 10. The elongated handle 13 may be provided with an adaptable tip portion 41 for connection to a fluid source, such as a Water Pik. While not shown, the dental flosser could in lieu of being attached to a fluid source, be attached to a battery charged source and function in the same fashion as an electric toothbrush. All of these various modifications of the other end of the dental flosser are well within the scope of the present invention. During operation of the embodiment of FIG. 8, a user may place the bifurcated flosser head in his mouth locating the dental floss 37 between two adjacent teeth. He then commences reciprocating motion of the floss in a seesaw manner across the teeth while at the same time moving the floss from bottom to top. At the same time, the water line can be actuated from the water source and cause a fluid to begin flowing through the cavity 42 which in turn will exit directly above the flossing element and achieve effective cleaning by simultaneous and combined action of the floss and hydraulic pressure. The major features of this type of arrangement are speed, ease of use and the simplicity of what would normally be a most complex operation.

Figure 9:
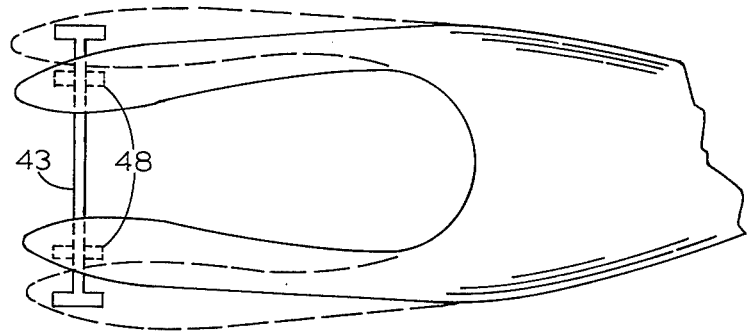
FIG. 9 is a fragmentary top view of a modified bifurcated flosser head and shows the spaced arms as being drawn together to allow a scrubbing element to be quickly slipped over the bifurcations.

Referring now to FIGS. 9 and 10, another embodiment is illustrated wherein a unique scrubbing element 43 is used as a cleaning element in lieu of dental floss. In order to adapt the bifurcated flosser head to receive the unique scrubbing element 43, the bifurcated arms 27 and 28 are provided with recessed indentations 48, which preferably are triangular in nature and which are only provided on the extreme outer extremities of the spaced arms. The scrubbing element 43 in turn, is provided with triangular end portions 46 and 47. By virtue of providing the bifurcated flosser head with a reduced cross-section 29, one may bias the spaced arms 27 and 28 together in order to insert the scrubbing element 43 as illustrated in FIG. 9. Such an embodiment allows the unique scrubbing element 43 to be easily and quickly slipped under the bifurcated ends 27 and 28, so that when the bifurcated ends are released, the bifurcated ends resume their original position and the scrubbing element 43 becomes tightly stretched and secured in the flosser head. The scrubbing element 43 is provided with a raised pattern or texture 45, which facilitates the cleaning of the teeth of debris and dental plaque. As described above in the description of the embodiment FIG. 8, it is well within the scope of this invention to include an interior fluid line in the dental flosser, whether the cleaning element employed is dental floss, such as illustrated in FIG. 3, or a scrubbing element as illustrated in FIG. 10. In both cases, the interior fluid line 42 is located within the interior of the elongated handle 13 and an opening 49 is provided directly above the cleaning element. Such an arrangement allows the embodiment of FIG. 10 to achieve an effective removal of debris and dental plaque by simultaneous and combined action of the scrubbing element and hydraulic pressure.

From the foregoing, it will be apparent that I have provided a dental flosser which is novel, highly versatile, simple and durable in construction, economical to manufacture and extremely effective in the cleaning and removal of debris and dental plaque from the teeth.

It is believed that the present invention, its mode of construction, assembly and operation and many of the advantages attendant thereto, should be readily understood from the foregoing description and it should also be manifest, that while several preferred embodiments of the invention have been shown and described for illustrative purposes, the structural details are nevertheless capable of wide variations within the purview of the artisan. For example, if desired a dental floss cutter could be provided on the elongated handle to enable one to quickly cut the dental floss. Also, a notch could be provided in the handle for hanging the dental flosser from a hook or a bracket. Also, the removable floss spool assembly could be eliminated and the dental flosser comprised of two detachable portions, which could easily be transported by the user in a carrying case.

It is believed that the present invention, its modus operandi, and many of the advantages attended thereto should be understood from the foregoing without further description. It should also be manifest that the present invention is capable of wide variations within the purview of the invention as defined in the appended claims.

The embodiment of the invention in which an exclusive property right is claimed is defined as follows:

I claim:

1. A dental flosser for cleaning and removing debris and dental plaque from the opposed surfaces of adjacent teeth comprising in combination an elongated handle having a longitudinal axis, a bifurcated head provided integrally at one end of said handle, and including a pair of downwardly, extending spaced and curved arms having concaved and notched extremities for receiving a length of dental floss, and floss anchoring means comprising a button affixed to the top surface and at the base of the elongated handle, said floss anchoring means having an undersurface which is tapered outward from its center, and a bulbed fulcrum portion being formed as an integral protrusion on the bottom surface of the elongated handle, said fulcrum portion being directly disposed on the opposite face of the elongated handle from the floss anchoring button, whereby during the cleaning operation the bulbed fulcrum portion may be seated upon an adjacent tooth and allowed to rock in an up and down or rotational fashion on the tooth such that a length of floss bridging the spaced arms may project onto the backside of the next back molar to clean the entire surface above and below the gum margin, and wherein said floss anchoring means is capable of positively securing a length of dental floss between the spaced arms by virtue of the ends being wrapped around one side of the floss anchoring means and pulled tightly transverse to the longitudinal axis of the dental flosser, said spaced arms having interior tip surface portions which are flared outwardly from the longitudinal axis of the dental flosser to protect the gums from injury when a length of floss bridging the spaced arms is engaged between adjacent teeth during the cleaning operation.

2. A dental flosser as defined in claim 1, wherein the notched extremities comprise an improved slit configuration at the outer front end of each spaced arm, said slit configuration comprising a slit at the outer front end of the spaced arms which terminates at its inner end in an enlargement, and further wherein a pair of diagonal grooves are provided on the exterior surface of the respective spaced arms adjacent to the base of the elongated handle to guide and support a length of floss when in use.

3. A dental flosser as defined in claim 1, wherein the other end of the elongated handle includes an integral toothbrush portion, and wherein the elongated handle is provided with a centrally located cavity having indentations formed at the opposite ends of the cavity for receiving a removable floss spool assembly.

4. A dental flosser as defined in claim 1, wherein an interior cavity is provided along the longitudinal axis of the elongated handle to form a fluid line for hydraulic pressure, said cavity extending from the other end to the bifurcated head of the dental flosser, said bifurcated head having an opening directly above the notched extremities, said fluid line being adapted for connection to a fluid source and providing a more effective cleaning of the teeth by simultaneous and combined action of the flosser and hydraulic pressure.

5. A dental flosser as defined in claim 1, wherein the spaced arms are provided with recessed indentations on the outer side peripheral areas, and further wherein a mechanical scrubbing element is securely held between the spaced arms.

6. A dental flosser as defined in claim 4, wherein the removable floss spool assembly comprises a detachable lid portion to which a bobbin of floss may be secured on the under-surface of the detachable lid, said detachable lid having securing means on the respective ends thereof so as to cooperate with the indentations at the respective ends of the centrally located cavity to securely position the removable floss spool assembly therein.

7. A dental flosser as defined in claim 5, wherein the scrubbing element is provided with triangular end portions, and wherein the recessed indentations of the spaced arms are triangular so as to cooperate with and securely receive the triangular end portions of the scrubbing element in a coupling arrangement.

8. A dental flosser as defined in claim 7, wherein the spaced arms are provided with a reduced cross-section adjacent to their attachment to the base of the elongated handle, so as to enable the spaced arms to be biased together during the installation of the scrubbing element, so that when the bifurcated ends are released, the bifurcated ends resume their original position and the scrubbing element is stretched tightly and secured between the bifurcated ends.

9. A dental flosser for cleaning and removing debris and dental plaque from the opposed surfaces of adjacent teeth comprising in combination an elongated handle having a longitudinal axis, a bifurcated head provided integrally at one end of said handle, and including a pair of downwardly, extending spaced and grooved arms having concaved and notched extremities that are adapted to receive a length of dental floss, and floss anchoring means comprising a button affixed to the top surface and at the base of the elongated handle, said floss anchoring means having an undersurface which is tapered from its center outwardly and having an underscored surface, and a bulbed fulcrum portion being integrally formed at the base of the elongated handle on the bottom surface of the handle, said spaced arms having interior tip surface portions which are flared outwardly from the longitudinal axis of the dental flosser, said spaced arms being provided with a reduced cross-section adjacent to this attachment to the base of the elongated handle to provide more flexibility of the spaced arms, diagonal grooves being provided on opposite exterior surface of the respective space arms to guide and support dental floss when it is threaded through the outer extremities of the spaced arms and both ends of which are secured around the same side of the floss anchoring means, and said floss being pulled tightly transverse to the longitudinal axis of the dental flosser.

* * * * *